(12) United States Patent
Torii

(10) Patent No.: US 6,641,528 B2
(45) Date of Patent: Nov. 4, 2003

(54) BENDING PART OF ENDOSCOPE

(75) Inventor: Yuichi Torii, Saitama (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 41 days.

(21) Appl. No.: 09/946,595

(22) Filed: Sep. 6, 2001

(65) Prior Publication Data

US 2002/0032371 A1 Mar. 14, 2002

(30) Foreign Application Priority Data

Sep. 8, 2000 (JP) ........................................ 2000-272969

(51) Int. Cl.$^7$ ................................................. A61B 1/00
(52) U.S. Cl. ........................ 600/142; 600/146; 600/149
(58) Field of Search ................................. 600/141, 142, 600/146, 149

(56) References Cited

U.S. PATENT DOCUMENTS

| | | | | |
|---|---|---|---|---|
| 4,108,211 A | * | 8/1978 | Tanaka | 600/142 |
| 4,432,349 A | * | 2/1984 | Oshiro | 600/141 |
| 4,726,355 A | * | 2/1988 | Okada | 600/114 |
| 5,394,864 A | * | 3/1995 | Kobayashi et al. | 600/146 |
| 5,704,898 A | * | 1/1998 | Kokish | 600/141 |
| 5,749,828 A | * | 5/1998 | Solomon et al. | 600/141 |
| 6,482,149 B1 | * | 11/2002 | Torii | 600/142 |

FOREIGN PATENT DOCUMENTS

JP          Y2 58-46801           10/1983

* cited by examiner

*Primary Examiner*—Linda C. M. Dvorak
*Assistant Examiner*—Jocelyn Ram
(74) *Attorney, Agent, or Firm*—Oliff & Berridge, PLC

(57) ABSTRACT

The bending part of an endoscope is constructed in which plural joint rings are connected with each other. The adjacent joint rings are rotatably connected with rivets after overlapping a connecting part with another connecting part. A guide hole is formed at the inner head of the rivet, and a bend-control wire is inserted through the guide hole whereby the bend-control wire is guided. A notch and a hole are formed at the end and the base of the connecting part, respectively; therefor the bend-control wire is prevented from coming into contact with the connecting part.

4 Claims, 9 Drawing Sheets

F I G. 8 (a)
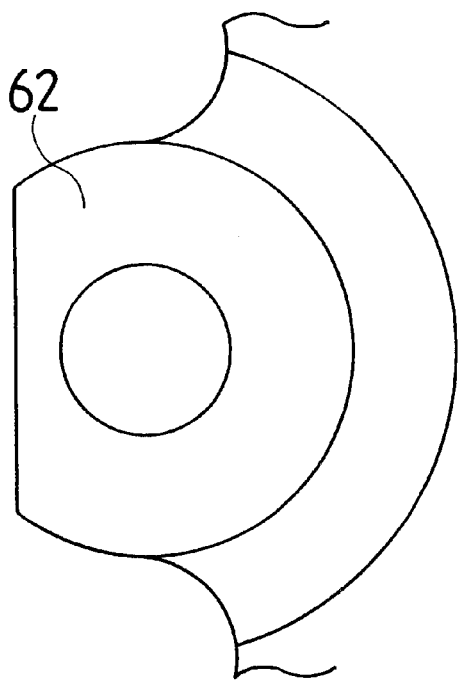
F I G. 8 (b)
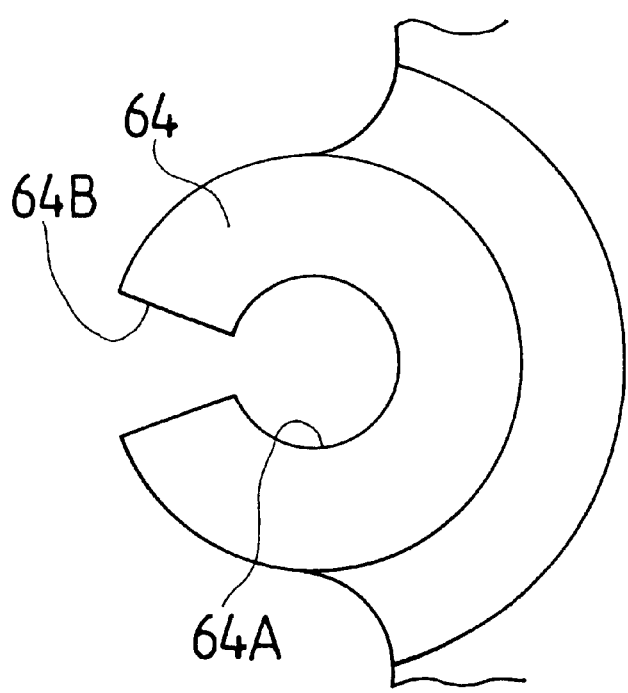

BENDING PART OF ENDOSCOPE

BACKGROUND OF THE INVENTION

1. Field of the Invention

The present invention relates to a bending part which is provided at an insertion part of an endoscope.

2. Description of the Related Art

A bending part which is provided at an insertion part of an endoscope is constructed by connecting plural joint rings with rivets. Japanese Utility Model Publication No. 58-46801 discloses a structure of a bending part shown in FIG. 11, in which inner heads of rivets 1 protrude from inner peripheral faces of joint rings 2, and guide holes 3 are formed in the inner heads of the rivets 1. Each of bend-control wires 4 for controlling the bend of the bending part is inserted through the guide holes 3, and is connected with a pulley within a hand control part. The bend-control wires 4 enable bend control of the bending part by rotating control knobs provided to the axes of the pulleys.

Such conventional structure of the bending part has a problem in that the bend-control wires 4 sometimes come into contact with the joint rings 2 when the bending part operates to strongly bend. If the bend-control wire 4 is in contact with the joint ring 2, the control response becomes poor and also the bend-control wire 4 may be damaged.

The problem can be solved by guiding the bend-control wires at positions away from the inner peripheral faces of the joint rings, but in that case the rivets must protrude more from the inner peripheral faces of the joint rings. When using the structure with the more-protruding rivets, the following facts should be considered. Due to a diameter of the insertion part of an endoscope is made smaller, a diameter of the joint rings constituting the bending part has been smaller, and a filling rate (a filling density) within the bending part increases, since sizes (sectional diameters) of contents, which may be various tubes, cables, etc., in the bending part cannot be made very small. Moreover, since the rivets for connecting the joint rings also serve as guides for the bend-control wires, positions at which the rivets are arranged are limited, and the rivets cannot be arranged without interference with the contents. As a result, if the rivets greatly protrude, they block the contents and the blocking causes difficulty in arrangement of the contents and may further cause damaging of the contents. Although protection members are available for preventing such damage, addition of the protection members within the bending part further increases the filling rate.

SUMMARY OF THE INVENTION

The present invention has been developed in view of the above-described circumstances, and has as its object the provision of a structure of a bending part of an endoscope which can prevent contact of a bend-control wire with joint rings.

In order to achieve the above-described object, the present invention is directed to a bending part of an endoscope, comprising: a plurality of joint rings, each of the plurality of joint rings having connecting parts at each of ends thereof; a plurality of rivets, each of the plurality of rivets connecting the connecting parts of adjacent two of the plurality of joint rings, each of the rivets having an inner head protruding from an inner periphery of each of the plurality of joint rings, the inner head having a wire guiding part; and a bend-control wire which is inserted in the bending part and guided with the wire guiding part of the inner head of each of the plurality of rivets, wherein at least one of the connecting parts of each of the plurality of joint rings has a cut portion for preventing contact with the bend-control wire.

According to the present invention, the bend-control wire is prevented from coming into contact with the connecting parts by providing the cut portions at the connecting parts of the joint rings; thus a control response improves and damage to the bend-control wire can be prevented.

In order to achieve the above-described object, the present invention is also directed to a bending part of an endoscope, comprising: a plurality of joint rings, each of the plurality of joint rings having connecting parts at each of ends thereof; a plurality of rivets, each of the plurality of rivets connecting the connecting parts of adjacent two of the plurality of joint rings, each of the rivets having an inner head protruding from an inner periphery of each of the plurality of joint rings, the inner head having a wire guiding part; and a bend-control wire which is inserted in the bending part and guided with the wire guiding part of the inner head of each of the plurality of rivets, wherein a distance in an insertion direction of the bend-control wire between an end of each of the connecting parts and each of the plurality of rivets connecting each of the connecting parts is shorter than a distance between the bend-control wire and each of the connecting parts.

According to the present invention, the distance in the insertion direction of the bend-control wire between the ends of the connecting parts and the rivets is shorter than the distance between the bend-control wire and the connecting parts; thus the bend-control wire can be prevented from coming into contact with the connecting parts. Therefore, the control response improves and the damage to the bend-control wire can also be prevented.

BRIEF DESCRIPTION OF THE DRAWINGS

The nature of this invention, as well as other objects and advantages thereof, will be explained in the following with reference to the accompanying drawings, in which like reference characters designate the same or similar parts throughout the figures and wherein:

FIGS. 8(a) and 8(b) are plan views showing connecting parts in shapes which are different from one in FIG. 6;

DETAILED DESCRIPTION OF THE PREFERRED EMBODIMENTS

Hereunder a preferred embodiment will be described in detail for a structure of a bending part of an endoscope according to preferred embodiments of the present invention in accordance with the accompanied drawings.

Figure 1:
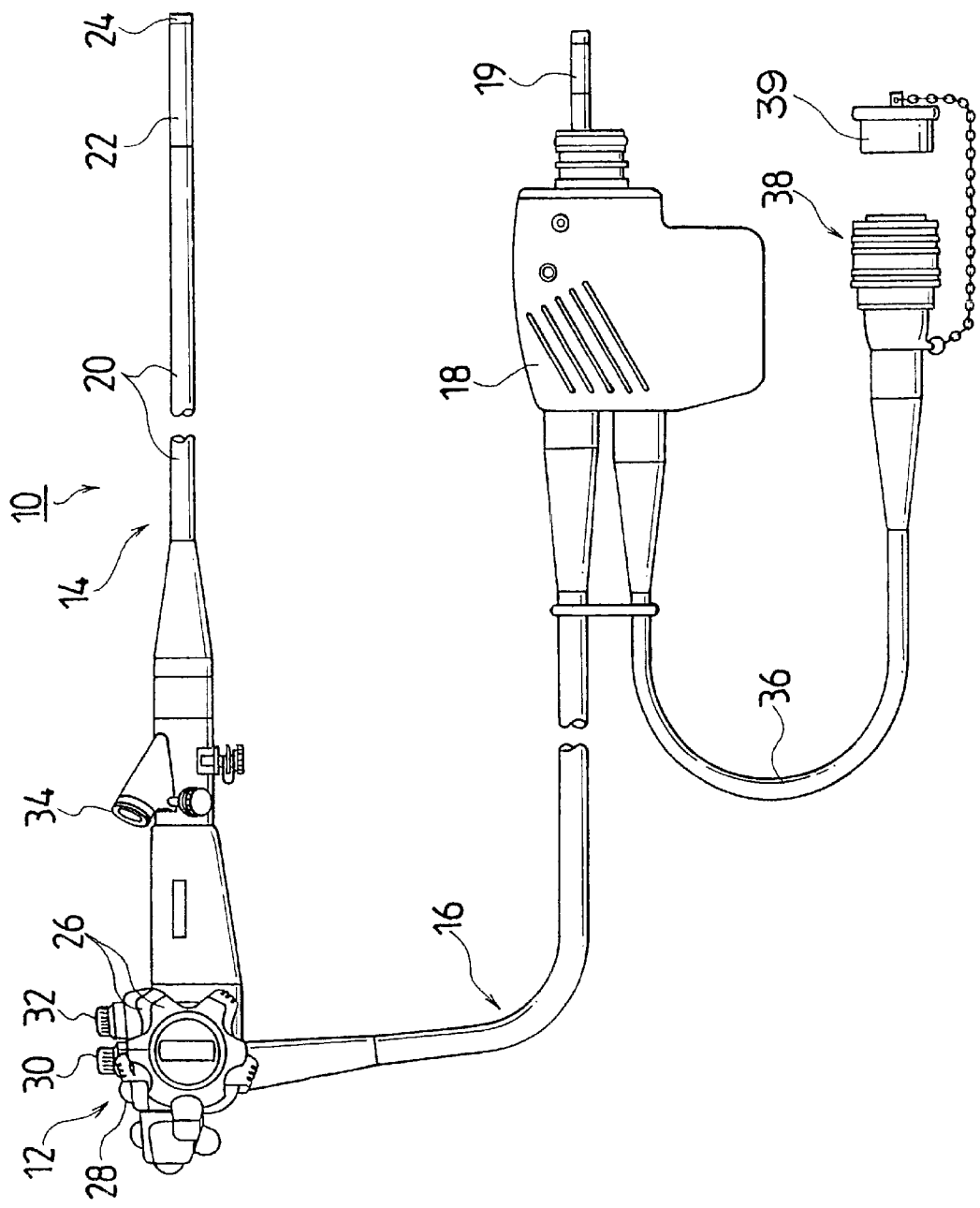
FIG. 1 is a view of an entire structure of an endoscope to which a bending part according to an embodiment of the present invention is applied.

An endoscope 10 in FIG. 1 to which a structure of a bending part according to an embodiment of the present invention is applied, has a hand control part 12, with which a base end of an insertion part 14 is connected. The insertion part 14 is constructed of a flexible part 20, a bending part 22, and a distal end part 24. The bending part 22 is remotely controlled by rotating a pair of control knobs 26, which are provided to the hand control part 12, whereby the distal end part 24 is directed toward desired directions.

The hand control part 12 is provided with a forceps channel 34, through which surgical instruments such as a forceps are inserted, a shutter-release button 28, a suction button 30, and an air/water supply button 32. Moreover, a light guide (LG) connector 18 is connected with the hand control part 12 via an LG flexible part 16. The LG connector 18 is provided with an LG stick 19, which is connected with a light source device (not shown), and is also connected with an electric connector 38 via a flexible tube 36. A cap 39 is attached to the electric connector 38.

Figure 2:
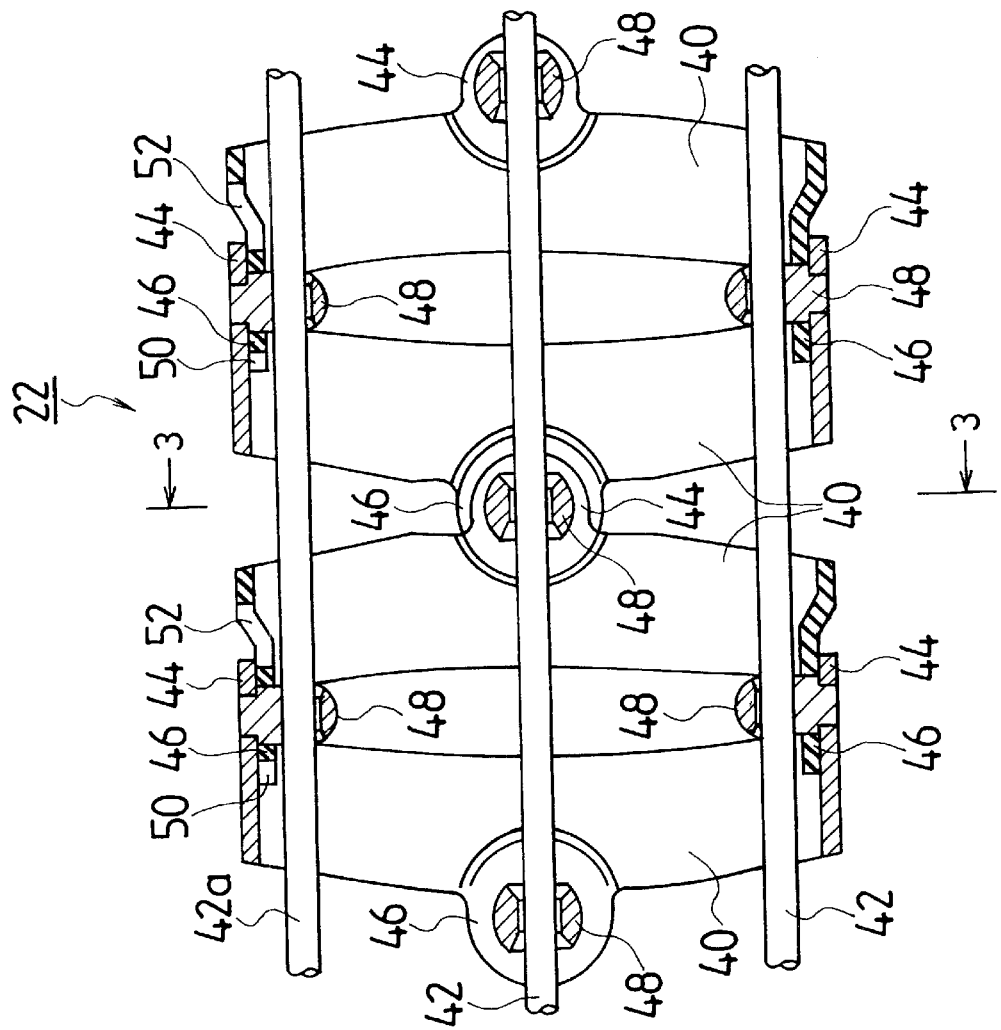
FIG. 2 is a vertical section view showing a structure of the bending part in FIG. 1.
Figure 3:
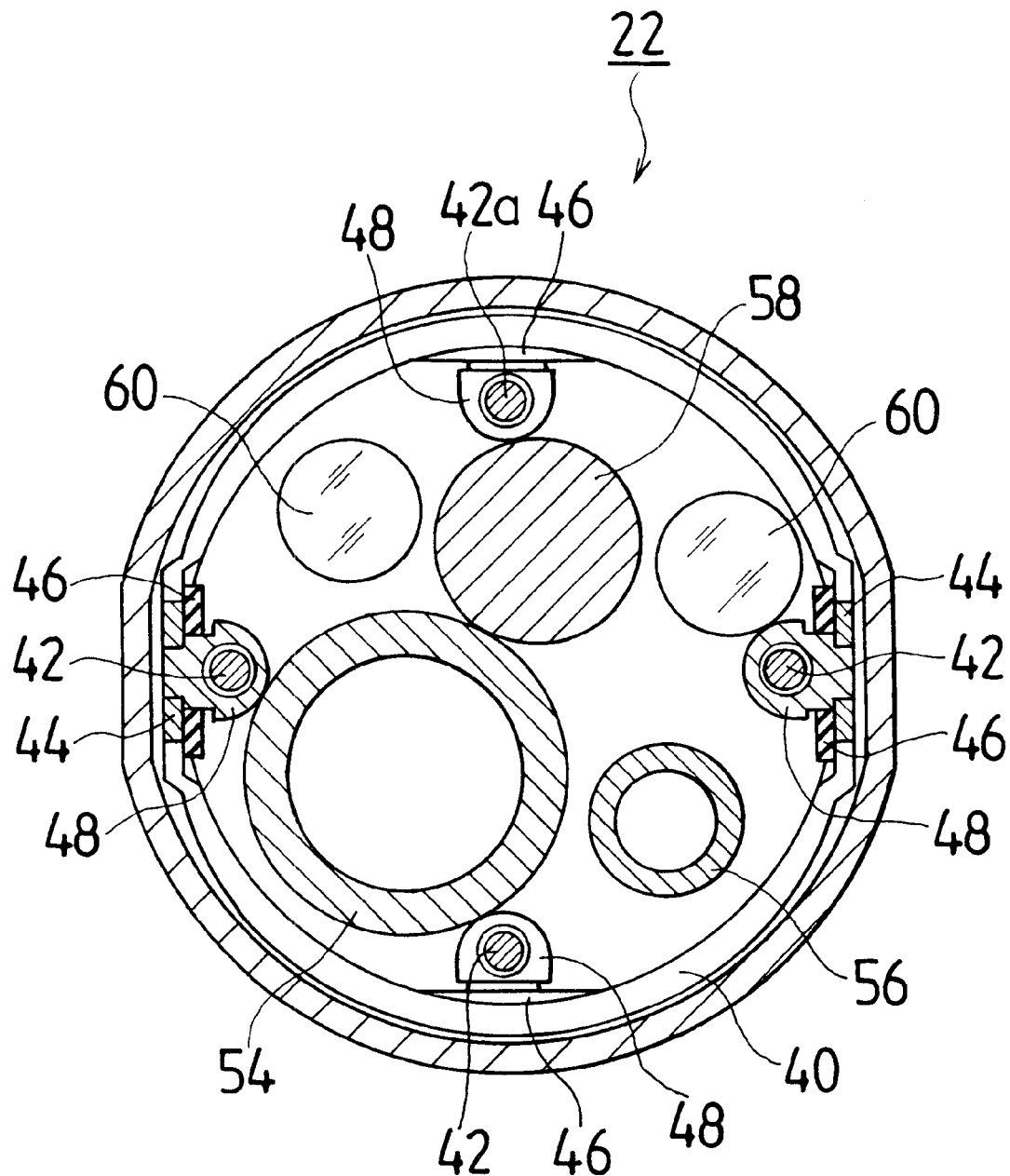
FIG. 3 is a section view of the bending part along a line 3—3 in FIG. 3.

As seen from FIGS. 2 and 3, the bending part 22 comprises a plurality of joint rings 40 connected to each other in an axial direction, and four bend-control wires 42 arranged in certain intervals along inner peripheral faces of the joint rings 40. The distal ends of the bend-control wires 42 are fixed to a distal end sleeve (not shown) that is secured at the distal end part 24 in FIG. 1, and the proximal ends of the bend-control wires 42 are connected with pulleys (not shown) that are rotated by the control knobs 26. The bend-control wires 42 are pushed and pulled when controlling the control knobs 26 so as to rotate the pulleys, and the bending part 22 is bent toward a desired direction.

Figure 4:
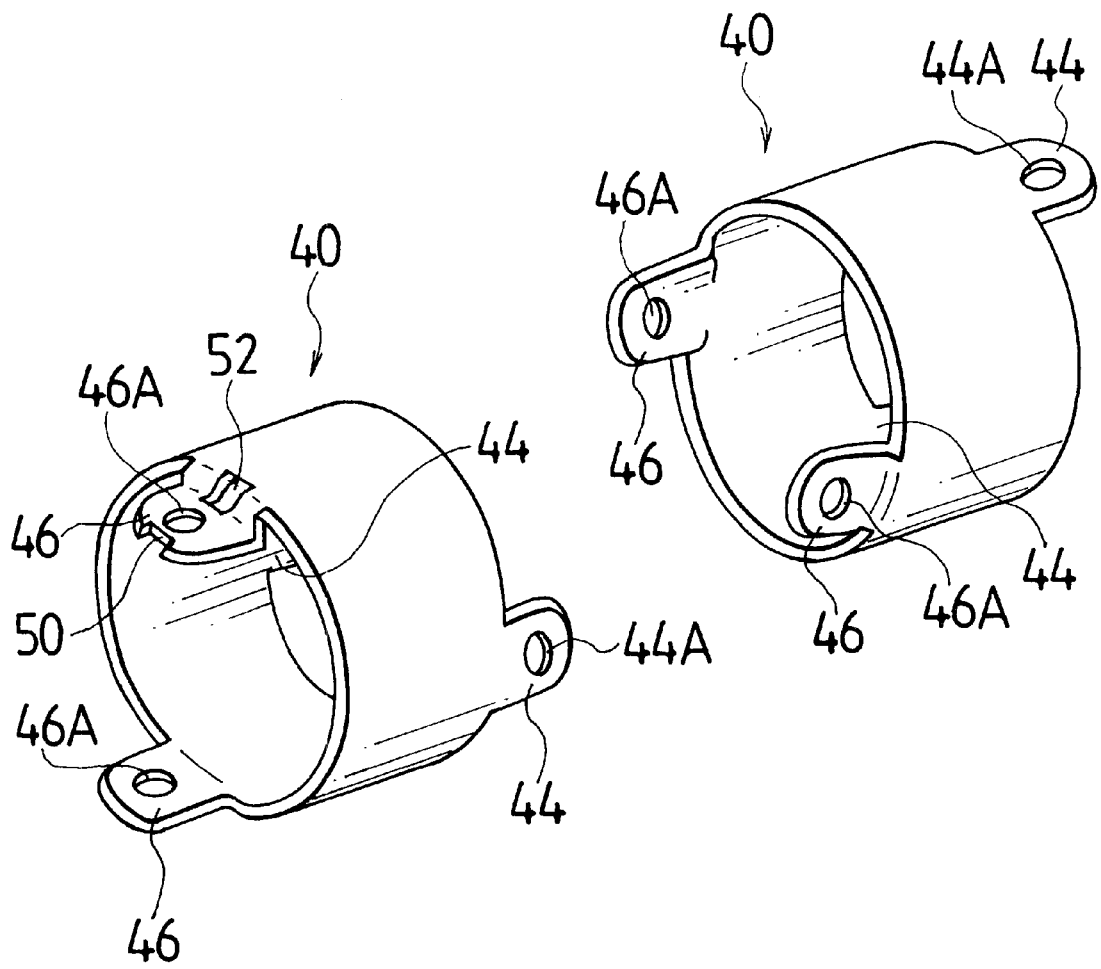
FIG. 4 is a perspective view of joint rings in FIG. 2.

As seen from FIG. 4, a pair of connecting parts 44 are formed on an end face of the joint ring 40 along the axial direction, and a pair of connecting parts 46 are formed on the other end face of the joint ring 40 along the axial direction. The pair of the connecting parts 44 are arranged at 180 degrees with respect to each other, and the pair of the connecting parts 46 are arranged at 180 degrees with respect to each other. The connecting part 44 and the connecting part 46 on the same joint ring 40 are arranged at 90 degrees with respect to each other. The connecting parts 46 are pressed into inside of the joint ring 44 by an amount of thickness of the joint ring 44, so that one connecting part 46 can be overlapped with one connecting part 44 of the next joint ring 40. Moreover, insertion holes 44A and 46A are formed in the connecting parts 44 and 46 for inserting rivets 46 shown in FIG. 5. After the connecting parts 44 and 46 are partially overlapped, the rivet 48 is inserted through the insertion holes 46A and 44A from inside of the joint rings 40, and the outer end of the rivet 48 is shaped into a head, whereby the connecting parts 44 and 46 are rotatably connected with each other.

A guide hole 48A is formed at the inner head of the rivet 48, and the bend-control wire 42 is inserted through the guide hole 48A to be guided.

Figure 5:
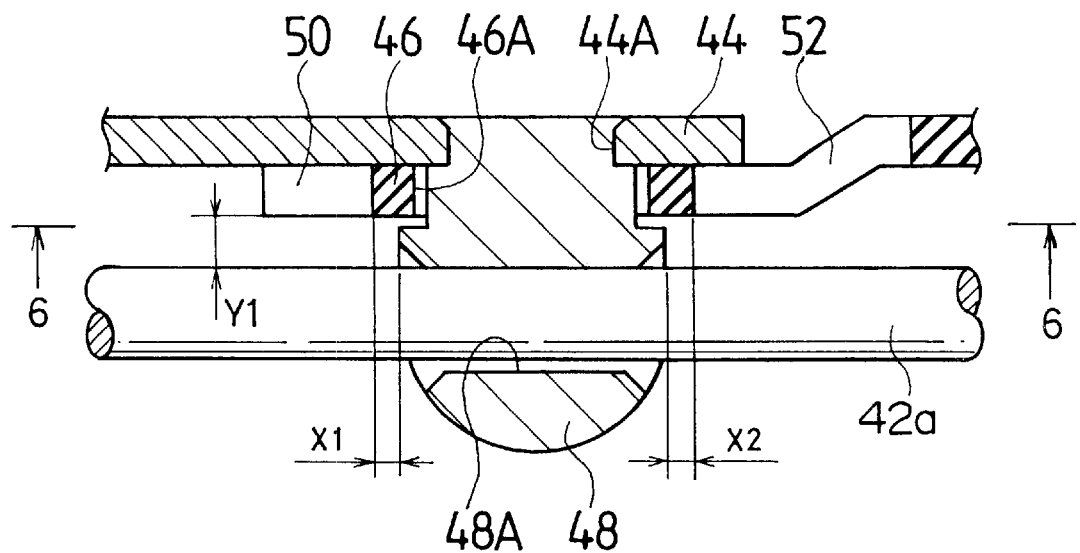
FIG. 5 is a vertical section view showing a connecting structure of the joint rings.
Figure 6:
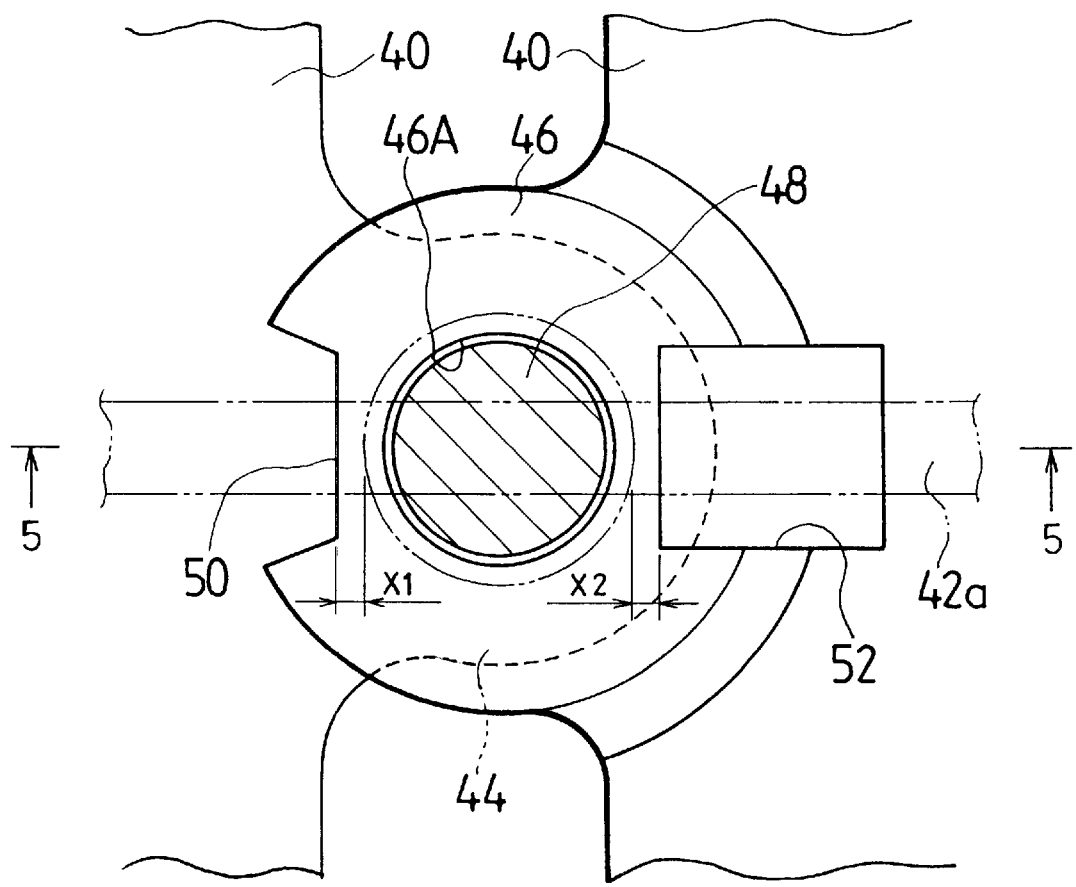
FIG. 6 is a section view along a line 6—6 in the connecting structure in FIG. 5.

The bending part 22 which is constructed as described above is especially bent strongly upward in FIG. 2, and one bend-control wire 42a arranged at the top side in FIG. 2 has hence a wider moving range than that of other bend-control wires 42, so that the bend-control wire 42a tends to contact with the connecting parts 46. In order to cope with this problem, each of the connecting parts 46 that are adjacent to the bend-control wire 42a has a cut portion or a notch 50 at the end of the connecting part 46 and a cut portion or a hole 52 at the base of the connecting part 46 as shown in FIGS. 5 and 6. A distance X1 between the end of the notch 50 and the rivet 48 is shorter than a distance Y1 between the connecting part 46 and the bend-control wire 42. A distance X2 between the end of the hole 52 and the rivet 48 is shorter than the distance Y1 between the connecting part 46 and the bend-control wire 42.

Now, an operation will be described of the structure of the bending part which is constructed as described above.

Figure 7:
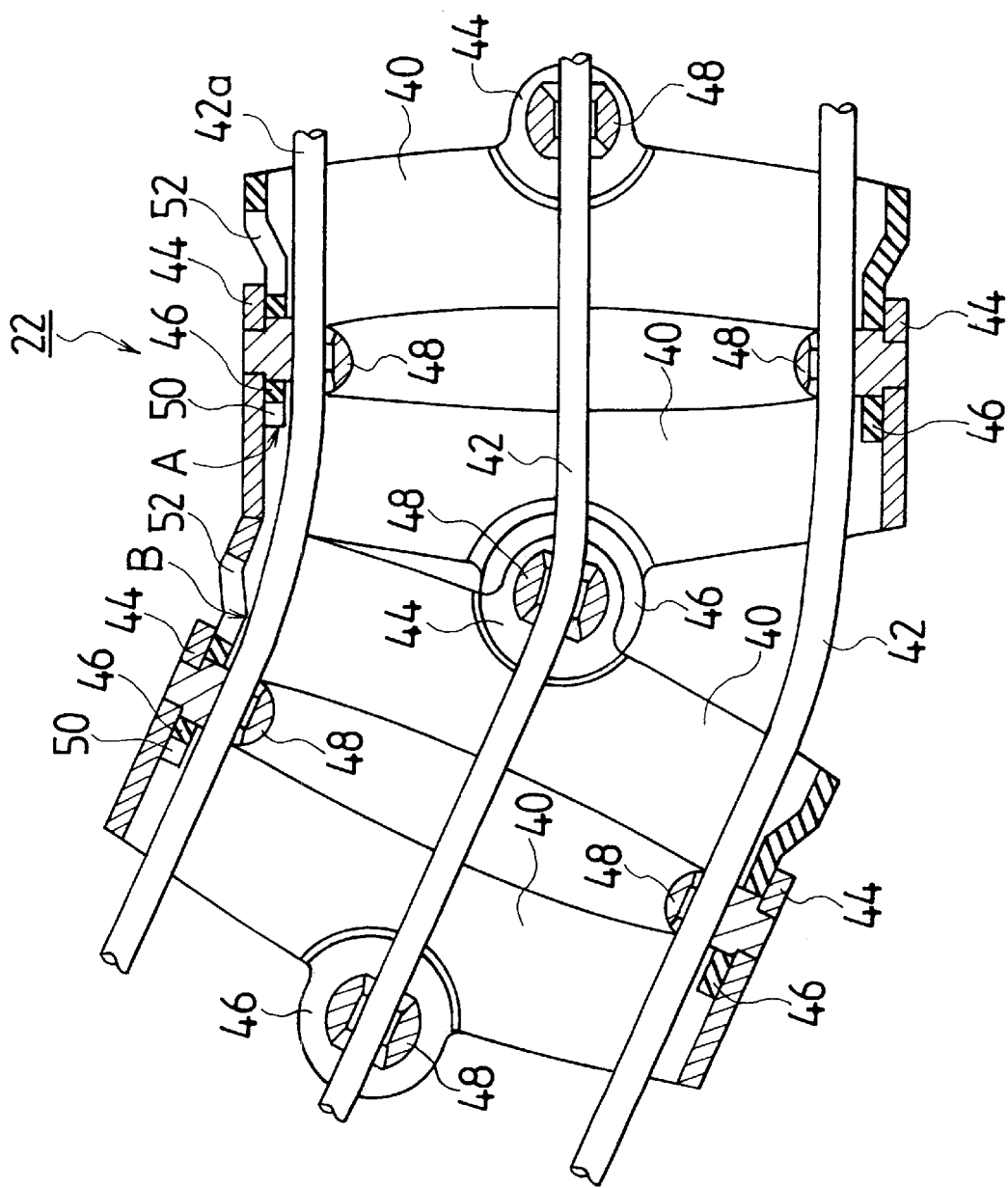
FIG. 7 is a view showing an operation of the structure of the bending part.

As seen from FIG. 7, the bend-control wire 42a comes closer to the connecting part 46 when strongly bending the bending part 22. In the conventional structure, the bend-control wire 42 is in contact with the connecting parts 46 at points A and B in FIG. 7, which results in poor control response and damaging the bend-control wire 42. In contrast, the structure of the bending part in the present embodiment has the notches 50 and the holes 52 at the connecting parts 46; hence the bend-control wire 42 does not contact with the connecting parts 46 at the points A and B, so that damaging of the bend-control wire 42 can be prevented.

In the structure as described above, a distance of protrusion of the inner heads of the rivets 48 from the inner peripheral face of the joint rings 40 can be short, whereby the filling rate of the contents in the bending part 22 can be reduced. In other words, if the notch 50 and the hole 52, which are so formed as to have the short distance X1 in FIG. 5, the bend-control wire 42 and the connecting parts 46 do not contact with each other even though the distance Y1 between the bend-control wire 42 and the connecting parts 46 is short. Hence, the distance of protrusion of the inner head of the rivet 48 can be short by making the distance Y1 short, and the flexibility of arrangements of the contents in the bending part 22 improves. As shown in FIG. 3, the contents such as a forceps tube 54, an air and water supply tube 56, a signal cable 58, and light guides 60 are inserted through the bending part 22. Because of that, if the diameter of the joint rings 40 is reduced by reducing the diameter of the bending part 22 in the conventional structure, the contents in the bending part 22 may be pressed by the rivets 48 and damaged when bending the bending part 22. In contrast, the structure of the bending part in the present embodiment has an improved flexibility of arrangements of the contents; hence the contents are not pressed, and durability of the contents is improved. Further, since the protection members do not have to be attached to the rivets and the like, the bending part 22 without the protection members can be thinner without increasing the filling rate.

In the present embodiment, the notches 50 and the holes 52 are formed only at the connecting parts 46 that are adjacent to the bend-control wire 42a; however, the notches 50 and the holes 52 may be formed also at the connecting parts 46 that are adjacent to other bend-control wires 42.

Further, if the notches 50 and the holes 52 are formed at the connecting parts 46 where the contents are concentrated, an amount of protrusion of the rivets 48 can be decreased, whereby the contents can be prevented from blocking the rivets 48 as well as difficulty in arranging the contents.

Shapes of the notch 50 and the hole 52 are not limited to the ones mentioned in the present embodiment, and may have any shapes as far as they have cut portions that might contact with the bend-control wire 42. For example, the end of the connecting part 46 may be tapered. Alternatively, the end of a connecting part 62 may be cut straight as shown in FIG. 8(a); or a notch 64B connecting to an insertion hole 64A may be formed like a connecting part 64 shown in FIG. 8(b).

Figure 9:
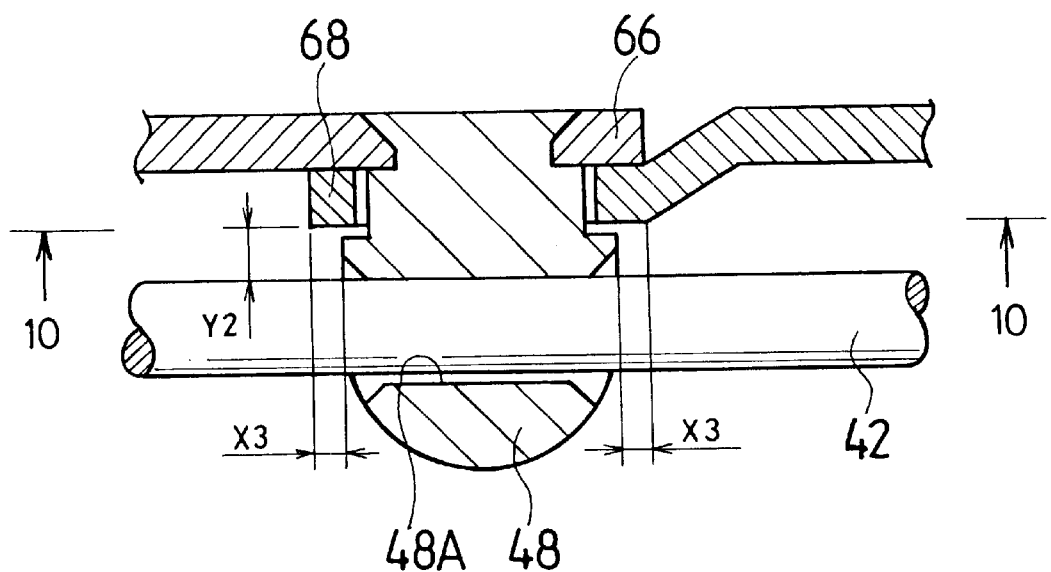
FIG. 9 is a vertical section view showing the connecting structure of the joint rings in a second embodiment.
Figure 10:
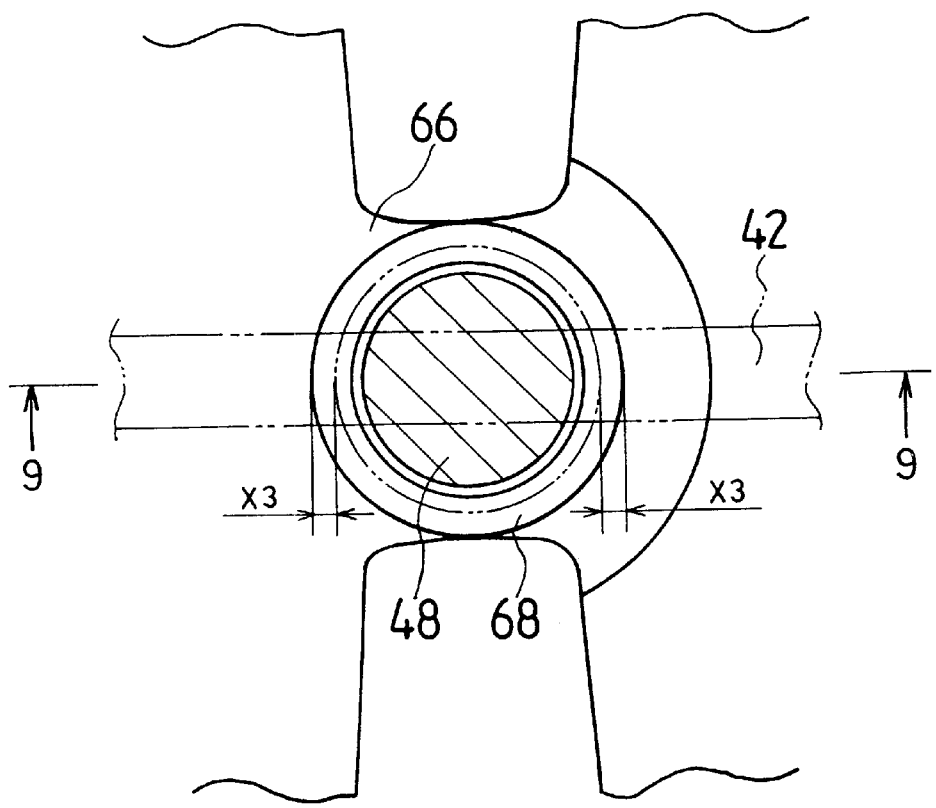
FIG. 10 is a section view along a line 10—10 in the connecting structure in FIG. 9.
Figure 11:
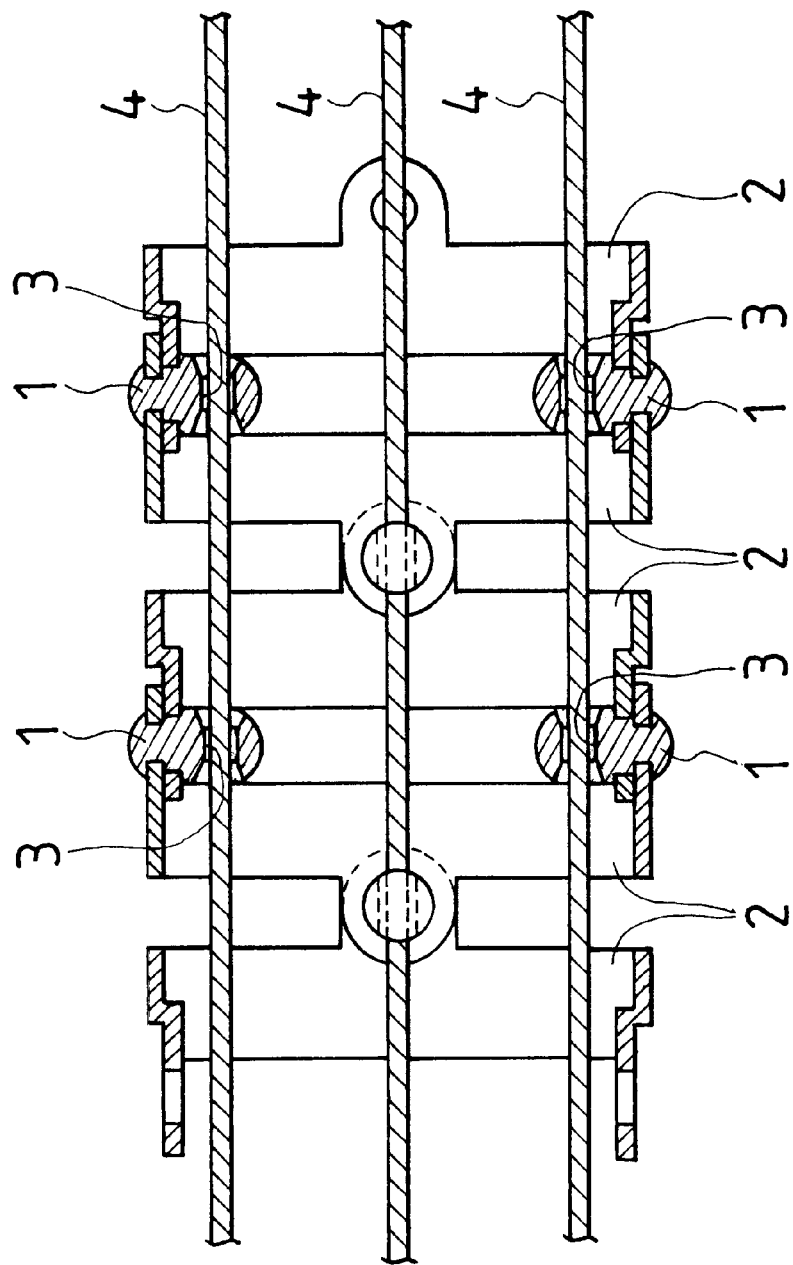
FIG. 11 is a section view showing the conventional structure of a bending part.

FIG. 9 is a side section view showing a structure of the bending part in a second embodiment, and FIG. 10 is a plan section view along a line 10—10 in FIG. 9. In these drawings, the same or similar elements or members as those mentioned in FIGS. 5 and 6 are assigned the same reference numbers, and the description on them will be omitted.

In the structure of the bending part in the second embodiment, connecting parts 66 and 68 are formed to be smaller in their entirety compared with the former connecting parts. Moreover, a distance X3 between the end of the connecting part 68 and the rivet 48 in the insertion direction of the bend-control wire 42 is shorter than the distance Y2 between the bend-control wire 42 and the connecting part 68. Because of that, the bend-control wire 42 does not contact with the connecting part 68 when operating the bending part 22 in the same manner as described in the first embodiment; thus the operability of the bending part 22 improves while preventing a damage to the bend-control wire 42.

As described hereinabove, according to the structure of the bending part of the endoscope according to the present invention, since contact of the bend-control wire with the connecting parts is prevented by providing cut portions at the connecting parts, control response improves while preventing damage to the bend-control wire.

Further, according to the present invention, the distance between the end of the connecting part and the rivet in the insertion direction of the bend-control wire is shorter than the distance between the bend-control wire and the joint ring. Therefore, the bend-control wire can be prevented from contacting with the connecting parts, and thereby improved control as well as prevention of damage to the bend-control wire are achieved.

Furthermore, because flexibility of arrangements of the contents improves, difficulty of arrangements due to blocking of the rivets and the contents is avoided, and thus the bending part can be thinner.

It should be understood, however, that there is no intention to limit the invention to the specific forms disclosed, but on the contrary, the invention is to cover all modifications, alternate constructions and equivalents falling within the spirit and scope of the invention as expressed in the appended claims.

What is claimed is:

1. A bending part of an endoscope, comprising:
   a plurality of joint rings, each of the plurality of joint rings having connecting parts at each of the ends thereof;
   a plurality of rivets, each of the plurality of rivets connecting the connecting parts of adjacent two of the plurality of joint rings, each of the rivets having an inner head protruding from an inner periphery of each of the plurality of joint rings, the inner head having a wire guiding part; and
   a bend-control wire which is inserted in the bending part and guided with the wire guiding part of the inner head of each of the plurality of rivets,
   wherein at least one of the connecting parts of each of the plurality of joint rings has a cut portion located to prevent contact of the bend-control wire with each joint ring during strong bending of the bending part.

2. The bending part as defined in claim 1, wherein:
   the cut portion comprises a notch formed at an end of the at least one of the connecting parts of each of the plurality of joint rings; and
   a distance between an end of the notch and each of the plurality of rivets connecting the at least one of the connecting parts is shorter than a distance between the bend-control wire and the at least one of the connecting parts.

3. The bending part as defined in claim 1, wherein:
   the cut portion comprises a hole formed at a base of the at least one of the connecting parts of each of the plurality of joint rings; and
   a distance between a peripheral edge of the hole and each of the plurality of rivets connecting the at least one of the connecting parts is shorter than a distance between the bend-control wire and the at least one of the connecting parts.

4. A bending part of an endoscope, comprising:
   a plurality of joint rings, each of the plurality of joint rings having connecting parts at each of the ends thereof that protrude radially inward from respective joint rings, wherein a distal portion extends along a longitudinal direction;
   a plurality of rivets, each of the plurality of rivets connecting the connecting parts of adjacent two of the plurality of joint rings, each of the rivets having an inner head protruding from an inner periphery of each of the plurality of joint rings, the inner head having a wire guiding part; and
   a bend-control wire which is inserted in the being part and guided with the wire guiding part of the inner head of each of the plurality of rivets,
   wherein a maximum distance along the longitudinal direction of the bend-control wire between both peripheral edges of the distal portion and each of the plurality of rivets connecting each of the connecting parts is shorter than a distance between the bend-control wire and each of the distal portions of the connecting parts to prevent contact of the bend-control wire with the joint rings during strong bending of the bending part.

* * * * *